United States Patent [19]

Yamane et al.

[11] Patent Number: 5,200,332

[45] Date of Patent: Apr. 6, 1993

[54] PROCESS FOR PREPARATION OF COPOLYMER

[75] Inventors: Tsuneo Yamane, Nagoya; Shunsaku Ueda, Toyoake; Shigeki Imagawa, Niigata; Torakazu Tahara, Niigata; Yoshiharu Tokunaga, Niigata; Hiroyuki Iesaka, Niigata; Teizi Urakami, Tokyo, all of Japan

[73] Assignee: Mitsubishi Gas Chemical Company, Inc., Tokyo, Japan

[21] Appl. No.: 759,919

[22] Filed: Sep. 13, 1991

[30] Foreign Application Priority Data

Sep. 14, 1990 [JP] Japan .................. 2-242605

[51] Int. Cl.$^5$ ............... C12P 7/62; C12R 1/05; C08G 63/06
[52] U.S. Cl. ................... 435/135; 435/247; 435/822; 435/829; 435/831
[58] Field of Search ............... 435/135, 247, 822, 829, 435/831

[56] References Cited

FOREIGN PATENT DOCUMENTS 150393 9/1982 Japan .
220192 12/1984 Japan .
269989 11/1988 Japan .
069622 3/1989 Japan .

OTHER PUBLICATIONS

"Systematic Bacteriology" Bergey's Manual vol. I pp. 140–142, 235–236, 325, 399 (1984) Krieg Editor Publisher Williams & Wilkens.
Bergeys Manual Systematic Bacteriology vol. 3, Staley Editor vol. III p. 1895 (1989) Publisher Williams & Wilkens.
"Internat. Journal Systematic Bact." Apr. 1984, pp. 188–201, vol. 34, No. 2, Urakami et al.
Internat. Jour. Syst. Bact. Apr. 1985, p. 209, vol. 35, No. 2.
Biotech Abs. 91-10051 EP-431883 (Jun. 1991) ICI.
Biotech Abs. 87-02762 EP-204442 (Dec. 1986) ICI.

*Primary Examiner*—Herbert J. Lilling
*Attorney, Agent, or Firm*—Sherman and Shalloway

[57] ABSTRACT

Disclosed is a process for the preparation of a copolymer, which comprises propagating cells of a bacterium having a capacity of producing poly-3-hydroxybutyrate mainly at a former stage, synthesizing and accumulating in the cells a copolymer comprising D-3-hydroxybutyrate and D-3-hydroxyvalerate by contacting the bacterium with a mixture of a carbon source utilizable by the bacterium and a primary alcohol having 3 to 7 carbon atoms, or with a primary alcohol having 3 to 7 carbon atoms, at a latter stage, and recovering the copolymer from the cells. According to this process, a copolymer comprising D-3-hydroxybutyrate and D-3-hydroxyvalerate can be manufactured in a large quantity at a low cost.

1 Claim, No Drawings

PROCESS FOR PREPARATION OF COPOLYMER

BACKGROUND OF THE INVENTION

(1) Field of the Invention

The present invention relates to a process for the preparation of a copolymer comprising D-3hydroxybutyrate (hereinafter referred to as "component B") and D-3-hydroxyvalerate (hereinafter referred to as "component V").

(2) Description of the Related Art

Poly-3-hydroxybutyrate (hereinafter referred to as "PHB") is a thermoplastic polymer, which is formed and accumulated as an energy-storing substance in cells of various microorganisms and shows an excellent biological decomposing property and an excellent living body compatibility, and therefore, the polymer attracts an attention as environment-preserving "clean" plastics and applications to a medical material such as a surgical thread or a broken bone-fixing material, or a gradually releasing system for gradually releasing a medicine or an agricultural chemical have been long investigated and expected. Recently, synthetic plastics have raised serious problems concerning environmental pollution and exhaustion of natural resources, and therefore, PHB has attracted attention as biopolymer not depending on petroleum. However, the melting point of PHB is close to the heat decomposition and PHB is brittle, and because of these defects, PHB can hardly be practically used.

Investigations have been made in the art for solving these problems, and polymers comprising component B and component V, which have a reduced melting point, an improved softness and an improved processability, and processes for the preparation of these polymers have been proposed (see Japanese Kokai Patent Publication No. 57-15093, Japanese Kokai Patent Publication No. 59-220192, Japanese Kokai Patent Publication No. 63-269989 and Japanese Kokai Patent Publication No. 01-69622). In these patent publications, there are processes in which copolymers are prepared by contacting cells of *Alcaligenes eutrophus* with a mixture of glucose-propionic acid, glucose-isobutyric acid and glucose-valeric acid under propagation-restricting conditions as attained by limiting nitrogen or phosphorus. These processes, however, are industrially disadvantageous because the manufacturing cost is high.

Accordingly, the present inventors made investigations with a view to developing a process capable of producing a copolymer comprising component B and component V more stably at a low manufacturing cost, and as the result, the present inventors have now completed the present invention.

SUMMARY OF THE INVENTION

While the present inventors made investigations with a view to developing a process of accumulating a copolymer comprising component B and component V by using a bacterium having a capacity of producing PHB, the present inventors found that if under propagation-restricting conditions this bacterium is contacted with a mixture of a carbon source utilizable by the bacterium and a primary alcohol having 3 to 7 carbon atoms, or with a primary alcohol having 3 to 7 carbon atoms, a copolymer comprising component B and component V can be accumulated in cells. The present invention has now been completed based on this finding.

More specifically, in accordance with the present invention, there is provided a process for the preparation of a copolymer, which comprises propagating cells of a bacterium having a capacity of producing poly-3-hydroxybutyrate mainly at a former stage, synthesizing and accumulating in the cells a copolymer comprising D-3-hydroxybutyrate and D-3-hydroxyvalerate by contacting the bacterium with a mixture of a carbon source utilizable by the bacterium and a primary alcohol having 3 to 7 carbon atoms, or with a primary alcohol having 3 to 7 carbon atoms, at a latter stage, and recovering the copolymer from the cells.

The component B and component V contained in the copolymer of the present invention are represented by the formula $-OCH(CH_3)CH_2CO-$ and the formula $-OCH(C_2H_5)CH_2CO-$, respectively.

Any of bacteria having a capacity of producing PHB can be used in the present invention without any limitation. For example, there can be mentioned bacteria belonging to genera *Pseudomonas, Alcaligenes, Athiorhodium, Azotobacter, Spirillum, Methylobacterum, Hypomicrobium, Ancylocater, Xanthobacter, Paracoccus, Rhizobium, Bradyhizobium, Bacillus, Nocardia, Corynebacterium, Rhodococcus* and *Azodobacter*. As typical instances of species belonging to these genera, there can be mentioned *Pseudomonas putida, Pseudomonas lemonnieri, Pseudomonas oleovorans, Pseudomonas facilis, Alcaligenes eutrophus, Alcaligenes is. Alcaligenes ruhlandii, Alcaligenes latus, Alcaligenes aquamarinus, Azotobater chroococcum, Azotobacter vinelandii, Methylobacterium extorquens, Methylobacterium organophilum, Methylocaterium mesophilicum, Methylobacterium rhodinum, Methylobacterium radiotolerans, Methylobacterium fujisawaense, Methylocaterium rhodesianum, Methylobacterium zatmanii, Hyphomicrobium vulgare, Hyphomicrobium aestuarii, Hyphomicrobium hollandicum, Hyphomicrobium facilis, Hyphomicrobium zavarzinii, Hyphomicrobium methylovorum, Xanthobacter autotrophicus, Xanthobacter flauns, Paracoccus demitirificans, Paracoccus alcaliphilus, Paracoccus aminophilus, Paracoccus aminovorans, Paracoccus kourii, Rhizobium meliloti, Rhizobium leguminosarum, Bradyrhizobium japonicum, Bacillus megaterium, Nocardia lucida, Corynebacterium hydrocarboxydans,* and *Corynebacterium dioxydans, Azotobacter vinelandi,* and *Azotobacter vinelandi.*

In the present invention, cells containing the copolymer are obtained through the first step (former stage) mainly for preparing cells and the second step (latter stage) mainly for forming and accumulating the copolymer in the cells.

The preparation of cells at the first step (former stage) is accomplished by the customary culturing method for propagating a bacterium, and a culture medium and culturing conditions, by which the bacterium used can be propagated, are used.

In the culturing medium, any of carbon sources utilizable by the bacterium used can be used without any limitation. For example, there can be mentioned saccharides such as glucose and sucrose, sugar alcohols such as glycerol, sorbitol and mannitol, organic acids such as succinic acid, citric acid and acetic acid, alcohols such as ethanol, methanol and propanol, carbon compounds such as yeast extract, molasses, corn steep liquor and malt extract, and organic nitrogen-containing natural substances. Any of nitrogen sources utilizable by the bacterium used can be used without limitation. For example, there can be mentioned ammonia, urea, nitric acid, and organic nitrogen-containing substances such as yeast extract and malt extract. Furthermore, there can be used phosphates, potassium salts, sodium salts, nitrates, and salts of metals such as magnesium, iron, calcium, zinc, cobalt, copper and molybdenum.

The culturing conditions depend on the kind of the bacterium used, but in general, culturing is carried out at a temperature of 20° to 40° C., preferably 25° to 35° C., and a pH value of 6 to 10, preferably 6.5 to 9.5. The bacterium is aerobically cultured under these conditions. Air or oxygen is introduced into the culturing liquid and if necessary, the culturing liquid is stirred for dissolving oxygen effectively in the culturing liquid. The dissolved oxygen concentration is preferably at least 1 ppm.

If culturing is conducted outside the above conditions, propagation of the bacterium is relatively controlled, but also this feature is included in the scope of the present invention.

After cells have been obtained by culturing the bacterium at the first step, the process transfers to the second step. At the second step, a carbon source utilizable as energy source by the bacterium and a primary alcohol having 3 to 7 carbon atoms are added into the culture medium to synthesize and accumulate the target polymer in the cells under bacterium propagation-inhibiting conditions. As the means for controlling propagation of the bacterium, there can be adopted a method in which culture medium ingredients other than the carbon source, such as nitrogen and phosphoric acid, are restricted in the culture medium. More specifically, a culture medium to be used at the first step is determined, and a carbon source is sufficiently supplied and culturing is conducted while adjusting the temperature and the pH value. After propagation of the bacterium is reduced because of the lack of medium ingredients other than the carbon source and is then stopped, the second step is conducted. Furthermore, there can be adopted a method in which cells of the bacterium are separated and recovered from the culture liquid of the first step by filtration or solid-liquid separation, and the recovered cells are suspended in a new culture medium and the second step is then conducted. In each method, the culturing conditions, other than the composition of the culture medium, at the second step may be the same as or different from those adopted at the first step according to the kind of the bacterium used. As the carbon source utilizable by the bacterium at the second step, there can be used not only the same carbon source as used at the first step, but also a carbon source utilizable by the bacterium but not allowing propagation, that can be used as the energy source. As the primary alcohol having 3 to 7 carbon atoms, to be used at the second step, there can be mentioned n-propanol and n-amyl alcohol (n-pentyl alcohol), and derivatives thereof.

In the case where this primary alcohol having 3 to 7 carbon atoms can be used as the energy source by the bacterium, only the primary alcohol having 3 to 7 carbon atoms can be used and the carbon source need not be particularly used. It is sufficient if the amounts of the carbon source utilizable as the energy source and the primary alcohol having 3 to 7 carbon atoms are enough to form and accumulate the target copolymer in cells, and the amounts are changed according to the kind of the bacterium used, the desired molar ratio between the components B and V in the copolymer, and the like. The total concentration of the carbon source and the primary alcohol is about 0.1 to 20 g, preferably about 0.2 to about 10 g, per liter of the culture liquid.

The molar ratio between the components B and V in the copolymer can be optionally changed by changing the ratio between the carbon source utilizable as the energy source and the primary alcohol having 3 to 7 carbon atoms. Generally, the molar ratio of the component V can be increased by increasing the proportion of the primary alcohol having 3 to 7 carbon atoms.

As the means for recovering the copolymer from the copolymer-containing cells, there can be adopted conventional methods such as a solvent extraction method using chloroform, dichloroform or sodium hypochlorite, and a method decomposing the cells with an enzyme.

EXAMPLES

The present invention will now be described in detail with reference to the following examples that by no means limit the scope of the invention.

EXAMPLE 1

Synthesis of copolymers was carried out by using *Methylobacterium fujisawaense* NCIB 12417, *Paracoccus derifrificans* ATCC 17441, *Alcaligenes eutrophus* ATCC 17687, *Alcaligenes eutrophus* NCIB 11597, and *Pseudomonas lemonnieri* ATCC 17989.

First Step

In 1 l of pure water were dissolved 5 g of polypeptone, 5 g of yeast extract and 5 g of glucose, and the pH value was adjusted to 7.0 and 50 ml of the solution was charged in a Sakaguchi flask. The solution was sterilized at 120° C. for 20 minutes to form a culture medium. The culture medium was inoculated with 1% by volume of a culture liquid of each strain preliminarily cultured at 30° C. for 24 hours in a culture medium as mentioned above, and reciprocating shaking culturing was conducted at 30° C. for 2 days. The culture liquid was subjected to centrifugal separation under 10,000 g for 10 minutes to collect cells.

Second Step

In 1 l of pure water were dissolved 1.6 g of $K_2HPO_4$, 2.4 g of $Na_2PO_4$, 0.2 g of $MgSO_4.7H_2O$, 0.3 mg of $CuSO_4.5H_2O$, 0.3 mg of $MnCl_2.4H_2O$, 18 mg of $FeC_6H_5O_2.xH_2O$, 18 mg of $CaCl_2.2H_2O$ and 3 mg of $ZnSO_4.7H_2O$, and the pH value was adjusted to 7.2 and the solution was sterilized at 120° C. for 20 minutes. The cells obtained at the first step was washed two times with 25 ml of the obtained solution, and the washed cells were suspended in the solution having the above composition. Then, 0.15 ml (0.3% by volume) of n-amyl alcohol was added to the suspension and reciprocating shaking culturing was conducted at 30° C.

The culturing of the latter stage was conducted for 50 hours, and cells were collected by a centrifugal separator, washed two times with pure water and dried at 60° C. About 40 mg of the dried cells were charged in a test tube equipped with a screw cap, and 1 ml of chloroform and 1 ml of an internal standard-incorporated methanol/sulfuric acid solution (internal standard 184 mg/100 ml of benzoic acid, sulfuric acid=3.5% by volume) were added and a heat treatment was carried out at 120° C. for 90 minutes to decompose the polymer contained in the cells and effect methyl-esterification. After termination of the reaction, 0.5 ml of pure water was added to the culture liquid and the mixture was violently stirred, and an organic layer was obtained by centrifugal separation. This organic layer was analyzed by the gas chromatography to determine the contents of the components B and V. From the sum of these contents, the content of the copolymer and the ratio of the component V in the copolymer were calculated. Furthermore, the concentration of n-amyl alcohol contained in the culture liquid at termination of the culturing of the second step and the pH value were examined. The obtained results are shown in Table 1.

Conditions for Gas Chromatography

Shimazu Gas Chromatogram GC-7AG
Column: Replex 400, chromosorb, AW-DMCS 10% (60 -80 mesh)
Column temperature: 160° C.
Inlet temperature: 250° C.

carried out at 30° C. for 50 hours. After 12 hours, 25 hours and 37 hours, the concentration of n-amyl alcohol contained in the culture liquid was measured, and n-amyl alcohol was added so that the concentration was 0.05% by volume. In case of *Methylobacterium fujisawaense*, the amount added of n-amyl alcohol was 0.01 ml after 25 hours and 0.005 ml after 37 hours. In case of *Paracoccus denitrificans* ATCC 17441 and *Alcaligenes eutrophus* ATCC 17697, the amount added of n-amyl alcohol was 0.025 ml after each of 12 hours, 25 hours and 37 hours, and in case of *Alcaliqenes eutrophus*, the amount added of n-amyl alcohol was 0.015 ml after each of 12 hours, 25 hours and 37 hours. In case of *Pseudomonas lemonnieri* ATCC 17989, the amount added of n-amyl alcohol was 0.01 ml after 37 hours.

The obtained results are shown in Table 2.

TABLE 2

| Strain | Total amount (% by volume) of added n-amyl alcohol | Copolymer content (% by weight) | Proportion (mole %) of component V | Culture liquid after culturing | |
|---|---|---|---|---|---|
| | | | | n-amyl alcohol (% by volume) | pH |
| *Methylobacterium fujisawaense* NCIB 12417 | 0.08 | 9.2 | 9.7 | 0.05 | 6.6 |
| *Paracoccus denitrificans* ATCC 17441 | 0.20 | 24.2 | 88.1 | 0.0 | 6.6 |
| *Alcaligenes eutrophus* ATCC 17697 | 0.20 | 12.8 | 56.9 | 0.02 | 6.7 |
| *Alcaligenes eutrophus* NCIB 11597 | 0.14 | 7.0 | 47.9 | 0.05 | 6.6 |
| *Pseudiminas lemonnieri* ATCC 17989 | 0.07 | 46.8 | 59.6 | 0.03 | 6.7 |

TABLE 1

| Strain | Copolymer content (% by weight) | Proportion (mole %) of component V | Culture liquid after culturing | |
|---|---|---|---|---|
| | | | n-amyl alcohol (% by volume) | pH |
| *Methylobacterium fujisawaense* NCIB 12417 | 12.3 | 2.4 | 0.12 | 5.0 |
| *Paracoccus denitrificans* ATCC 17441 | 8.7 | 76.4 | 0.14 | 5.0 |
| *Alcaligenes eutrophus* ATCC 17697 | 15.0 | 77.5 | 0.0 | 6.7 |
| *Alcaligenes eutrophus* NCIB 11597 | 16.8 | 29.9 | 0.0 | 6.7 |
| *Pseudomonas lemonnieri* ATCC 17989 | 3.2 | 0 | 0.22 | 6.8 |

EXAMPLE 2

The copolymer was synthesized in the same manner as described in Example 1 except that the amount of n-amyl alcohol added at the second step was changed as described below.

Namely, 0.025 ml (0.05% by volume) of n-amyl alcohol was added and reciprocating shaking culturing was

EXAMPLE 3

The copolymer was synthesized in the same manner as described in Example 1 except that 0.25 g of glucose (0.5% by weight) as the carbon source and 0.15 ml (0.3% by volume) of n-amyl alcohol were added at the second step.

The obtained results are shown in Table 3.

TABLE 3

| Strain | Copolymer content (% by weight) | Proportion (mole %) of component V | Culture liquid after culturing | | |
|---|---|---|---|---|---|
| | | | n-amyl alcohol (% by volume) | glucose (% by weight) | pH |
| *Methylobacterium fujisawaense* NCIB 12417 | 12.4 | 0.6 | 0.0 | 0.37 | 4.7 |
| *Paracoccus denitrificans* ATCC 17441 | 13.3 | 74.1 | 0.13 | 0.43 | 5.0 |
| *Alcaligenes europhus* ATCC 17697 | 9.9 | 62.2 | 0.01 | 0.20 | 5.5 |
| *Alcaligenes europhus* NCIB 11597 | 1.2 | 31.8 | 0.24 | 0.03 | 6.6 |
| *Pseudomonas lemonnieri* | 35.6 | 48.2 | 0.23 | 0.26 | 6.7 |

EXAMPLE 4

The copolymer was synthesized in the same manner as described in Example 3 except that the amount added of n-amyl alcohol was changed in the following manner.

Namely, 0.25 g (0.5% by weight) of glucose and 0.025 ml (0.05% by volume) of n-amyl alcohol were added and reciprocating shaking culturing was carried out at 30° C. for 50 hours. After 12 hours, 25 hours and 37 hours, the concentration of n-amyl alcohol in the culture liquid was measured, and n-amyl alcohol was added so that the concentration was 0.05% by volume. In case of *Methylobacterium fujisawaense* NCIB 12417, the amount of added n-amyl alcohol was 0.01 ml after 25 hours and 0.005 ml after 37 hours, and in case of *Paracoccus denitrificans* ATCC 17441, the amount of added n-amyl alcohol was 0.025 ml after each of 12 hours, 25 hours and 37 hours. In case of *Alcaligens eurphus* NCIB 17697, the amount of added n-amyl alcohol was 0.015 ml after 12 hours and 0.025 ml after each of 25 hours and 37 hours, and in case of *Alcaligenes eutrophus* NCIB 11597, the amount of added n-amyl alcohol was 0.005 ml after 12 hours and 0.015 ml of each of 25 hours and 37 hours. In case of *Pseudomona lemonnieri* ATCC 17989, the amount of added n-amyl alcohol was 0.015 ml after 37 hours.

The obtained results are shown in Table 4.

TABLE 4

| Strain | Total amount (% by volume) of n-amyl alcohol | Copolymer content (% by weight) | Proportion (mole %) of component V | Culture liquid after culturing | | |
|---|---|---|---|---|---|---|
| | | | | n-amyl alcohol (% by weight) | glucose (% by weight) | pH |
| *Methylobacterium fujisawaense* NCIB 12417 | 0.08 | 12.0 | 12.0 | 0.05 | 0.46 | 6.6 |
| *Paracoccus dinitrificans* ATCC 17441 | 0.20 | 34.1 | 50.1 | 0.0 | 0.26 | 6.0 |
| *Alcaligenes eutrophus* ATCC 17697 | 0.18 | 12.1 | 55.9 | 0.0 | 0.19 | 5.1 |
| *Alkaligenes eutrophus* NCIB 11597 | 0.12 | 16.8 | 29.9 | 0.05 | 0.09 | 6.6 |
| *Pseudomonas lemonnieri* ATCC 17989 | 0.08 | 17.4 | 47.4 | 0.04 | 0.23 | 6.7 |

EXAMPLE 5

The copolymer was synthesized by using *Alcaligenes eutrophus* NCIB 11597 or *Pseudomonas lemonnieri* ATCC 17989.

Namely, the copolymer was synthesized in the same manner as described in Example 3 except that the amount added of n-amyl alcohol was changed to 0.025 ml (0.05% by volume) at the second step.

The obtained results are shown in Table 5.

TABLE 5

| Strain | Copolymer Content (% by weight) | Proportion (mole %) of Component V |
|---|---|---|
| *Alcaligenes eutrophus* NCIB 11597 | 33.4 | 15 |
| *Pseudomonas lemonnieri* ATCC 17989 | 36.8 | 26 |

EXAMPLE 6

The copolymer was synthesized by using *Alcaligenes eutrophus* ATCC 17697. The influence of the concentration of n-amyl alcohol at the second step was examined.

The first step was conducted in the same manner as described in Example 3, and the second step was conducted in the same manner as described in Example 3 except that the concentration of n-amyl alcohol was adjusted to 0, 0.05, 0.1, 0.2, 0.3, 0.4 or 0.5% by volume, whereby a copolymer was synthesized. The pH value of the culture liquid after termination of the second step was examined.

The obtained results are shown in Table 6.

TABLE 6

| Amount (% by volume) of added n-amyl alcohol | Copolymer content (% by weight) | Proportion (molar ratio) of component V | ph Value after culturing |
|---|---|---|---|
| 0 | 0.9 | 0 | 6.7 |
| 0.05 | 1.4 | 58 | 6.6 |
| 0.1 | 4.9 | 60 | 6.6 |
| 0.2 | 11.4 | 64 | 6.5 |
| 0.3 | 17.5 | 68 | 6.6 |
| 0.4 | 4.8 | 90 | 6.5 |
| 0.5 | 1.0 | 51 | 5.7 |

EXAMPLE 7

The copolymer was synthesized by using *Methylobacterium extorquens* K (FERM BP-3548) (this strain was first deposited as *Protomonas extorquens*, but since *Protomonas extorquens* was changed to *Methylobacterium extorquens* by International Journal of Systematic Bacteriology, volume 35, page 209, 1985, the strain is expressed as *Methylobacterium extorquens*).

The synthesis was carried out in the same manner as described in Example 3 except that (1) 0.25 g (0.5% by weight) of glucose and 0.025 ml (0.05% by volume) of n-amyl alcohol (two times; at the start and after 25 hours culturing), (2) 0.25 g (0.5% by weight) of fructose and 0.025 ml (0.05% by volume) of n-amyl alcohol, (3) 0.25 g (0.5% by weight) of sucrose and 0.25 ml (0.05% by volume) of n-amyl alcohol, or (4) 0.25 g (0.5% by weight) of glycerol and 0.025 ml (0.05% by volume) of n-amyl alcohol were used as the carbon source at the second step.

The obtained results are shown in Table 7.

TABLE 7

| Carbon source | Copolymer content (% by weight) | Proportion (molar ratio) of component V | pH Value after culturing |
| --- | --- | --- | --- |
| (1) 0.5% by weight of glucose, 0.05% by volume × 2 of n-amyl alcohol | 13.3 | 78.6 | 5.5 |
| (2) 0.5% by weight of fructose, 0.05% by volume of n-amyl alcohol | 31.6 | 43.0 | 5.9 |
| (3) 0.5% by weight of sucrose, 0.05% by volume of n-amyl alcohol | 8.7 | 82.3 | 5.7 |
| (4) 0.5% by weight of glycerol, 0.05% by weight of n-amyl alcohol | 13.4 | 58.6 | 4.6 |

EXAMPLE 8

The copolymer was synthesized by using *Paracoccus denitrificans* ATCC 17441.

The synthesis was carried out in the same manner as described in Example 3 except that (1) 0.25 g (0.5% by weight) of glucose and 0.025 ml (0.05% by volume) of n-amyl alcohol (two times; at the start and after 25 hours' culturing), (2) 0.25 g (0.5% by weight) of fructose and 0.025 ml (0.05% by volume) of n-amyl alcohol, or (3) 0.25 g (0.5% by weight) of sucrose and 0.025 ml (0.05% by volume) of n-amyl alcohol were used as the carbon source at the second step.

The obtained results are shown in Table 8.

TABLE 8

| Carbon source | Copolymer content (% by weight) | Proportion (molar ratio) of component V | pH Value after culturing |
| --- | --- | --- | --- |
| (1) 0.5% by weight of glucose, 0.05% by volume × 2 of n-amyl alcohol | 49.1 | 47.1 | 6.5 |
| (2) 0.5% by weight of fructose, 0.05% by volume of n-amyl alcohol | 40.9 | 68.1 | 6.5 |
| (3) 0.5% by weight of sucrose, 0.05% by volume of n-amyl alcohol | 49.6 | 43.5 | 6.4 |

EXAMPLE 9

The copolymer was synthesized by using *Methylobacterium extorquens* K (FERM BP-3548) *Methylobacterium organophilum* ATCC 27886, *Methylobacterium fujisawaense* NCIB 12417, *Hyphomacrobium methylovorum* IFO 14180, *Xanthobacter autotrophicus* DSM 432, or *Paracoccus denitrificans* ATCC 17441.

First Step

In 1 l of pure water were dissolved 3.0 g of $(NH_4)_2SO_4$, 1.4 g of $KH_2PO_4$, 3.0 g of $Na_2HPO_4$, 0.2 g of $MgSO_4.7H_2O$, 0.2 g of yeast extract, 0.3 g of $NaHCO_3$, 0.03 mg of $CuSO_4.5H_2O$, 0.3 mg of $ZnSo_4.7H_2O$, 3 mg of $MnCl_2.4H_2O$, 0.18 mg of $FeC_6H_5O_2.xH_2O$, 0.18 mg of $CaCl_2.2H_2O$ and 10 ml of methanol, and the pH value was adjusted to 7.2. Then, 50 ml of the formed solution was charged in a Sakaguchi flask and sterilized at 120° C. for 20 minutes to form a culture medium.

The culture medium was inoculated with 1% by volume of a culturing liquid of each species obtained by conducting preliminary culturing at 30° C. for 3 days by using the above culture medium, and reciprocating shaking culturing was conducted at 30° C. for 2 days. The culture liquid was subjected to centrifugal separation under 10,000 g for 10 minutes to collect cells.

Second Step

In 1 l of pure water were dissolved 1.6 g of $K_2HPO_4$, 2.4 g of $N_2HPO_4$, 0.2 g of $MgSO_4.7H_2O$, 0.3 mg of $CuSO_4.5H_2O$, 0.3 mg of $MnCl_2.4H_2O$, 18 mg of $FeC_6H_5O_2 \cdot xH_2O$, 18 mg of $CaCl_2.2H_2O$ and 0.3 mg of $ZnSO_4.7H_2O$, and the pH value was adjusted to 7.2. The solution was sterilized at 120° C. for 20 minutes. The cells obtained at the first step were washed two times with 25 ml of the sterilized solution. Then, the cells were suspended in 50 ml of the solution having the above-mentioned composition, and 0.15 ml (0.3% by volume) of methanol and 0.025 ml of n-amyl alcohol were added to the suspension and reciprocating shaking culturing was carried out at 30° C. for 25 hours. Then, 0.15 ml of methanol and 0.025 ml of n-amyl alcohol were added again and reciprocating shaking culturing was carried out for 25 hours.

The culturing of the second step was thus conducted for 50 hours, and then, the content of the copolymer contained in the cells and the ratio of the component V in the copolymer were determined in the same manner as described in Example 1.

The pH value of the culture liquid after termination of the culturing was examined.

The obtained results are shown in Table 9.

TABLE 9

| Strain | Copolymer content (% by weight) | Proportion (molar ratio) of component V | pH Value after culturing |
|---|---|---|---|
| Methylobacterium extorquens K | 29.7 | 32 | 5.8 |
| Methylobacterium organophilum ATCC 27886 | 7.5 | 17 | 5.0 |
| Methylobacterium fujisawaense NCIB 12417 | 17.7 | 38 | 6.7 |
| Hyphomicrobium methylovorum IFO 14180 | 12.5 | 3 | 4.1 |
| Xanthobacter autrophicus DSM 432 | 16.2 | 12 | 6.5 |
| Paracoccus denitrificans ATCC 17441 | 53.2 | 71 | 6.6 |

EXAMPLE 10

The copolymer was synthesized by using *Methylobacterium extorquens* K. The influence of the amount of n-amyl alcohol added at the second step was examined.

The first step was conducted in the same manner as described in Example 1, and the second step was conducted in the same manner as described in Example 1 except that the concentration of n-amyl alcohol was adjusted to 0, 0.02, 0.04, 0.06, 0.08 or 0.10% by volume and after 25 hours, the same amount of n-amyl alcohol was added, whereby the copolymer was synthesized.

The obtained results are shown in Table 10.

TABLE 10

| n-Amyl alcohol concentration (% by volume) (twice added) | Copolymer content (% by weight) | Proportion (molar ratio) of component V | pH Value after culturing |
|---|---|---|---|
| 0 | 24.4 | 0 | 6.8 |
| 0.02 | 17.4 | 3 | 6.5 |
| 0.04 | 23.5 | 33 | 6.6 |
| 0.06 | 29.7 | 32 | 5.8 |
| 0.08 | 28.7 | 37 | 5.3 |
| 0.10 | 25.9 | 29 | 4.9 |

EXAMPLE 11

The copolymer was synthesized by using *Methylobacterium extorquens* K.

Step 1

In 1 l of pure water was dissolved 3.0 g of $(NH_4)_2SO_4$, 1.4 g of $K_2HPO_4$, 3.0 g of $Na_2HPO_4$, 0.2 g of $MgSO_4.7H_2O$, 0.2 g of yeast extract, 0.5 mg of $CuSO_4.5H_2O$, 5 mg of $MnCl_2.4H_2O$, 30 mg of $FeC_6H_5O_2.xH_2O$, 30 mg of $CaCl_2.2HO$, 5 mg of $ZnSO_4.7H_2O$ and 12 ml of methanol, and the pH value was adjusted to 7.2. Then, 200 ml of the obtained solution was charged in an Elrenmeyer flask having a capacity of 1 liter and was sterilized at 120° C. for 20 minutes to form a culture medium.

The solution was incubated with 1% by volume of the culturing liquid obtained by conducting preliminary culturing of the above-mentioned species by using the same culture medium as described above, and rotary shaking culturing was conducted at 30° C. for 54 hours. After termination of the logarithmic growth phase, the culture liquid was subjected to centrifugal separation under 10,000 g for 10 minutes to collect cells.

Second Step

In 1 l of pure water were dissolved 1.6 g of $K_2HPO_4$, 2.4 g of $Na_2HPO_4$, 0.2 g of $MgSO_4.7H_2O$, 0.8 g of $(NH_4)_2SO_4$, 0.3 mg of $CuSO_4.5H_2O$, 3 mg of $MnCl_2.4H_2O$, 18 mg of $FeC_6H_5O_2.xH_2O$, 18 mg of $CaCl_2.2H_2O$ and 3 mg of $ZnSO_4.7H_2O$, and the pH value was adjusted obtained solution was sterilized at 120° C. for 20 minutes, and the cells collected at the first step were washed two times with 100 ml of the obtained solution and suspended in 200 ml of the solution having the above-mentioned composition. Then, 1 g (0.5% by weight) of n-amyl alcohol and 1 g (0.5% by weight) of methanol were added to the suspension, and rotary shaking culturing was carried out at 30° C. for 48 hours. The methanol concentration was measured during the culturing, and if the methanol concentration became lower than 0.25% by weight, 1 g (corresponding to 0.25% by weight) of methanol was added. Thus, methanol was added three times during the culturing.

After the culturing, the amount of the copolymer contained in the cells, the contents of the components B and V and the proportion of the component V in the copolymer were determined in the same manner as described in Example 1.

As the result, it was found that the content of the copolymer was 31.5% by weight, the content of the component B was 14.1% by weight, the content of the component V was 17.4% by weight, and the proportion of the component V in the copolymer was 51 mole %.

As is apparent from the foregoing description, according to the present invention, a copolymer of D-3-hydroxybutyrate and D-3-hydroxyvalerate can be manufactured in a large quantity at a low cost.

We claim:

1. A process for the preparation of a copolymer comprising D-3-hydroxybutyrate and D-3-hydroxyvalerate which comprises cultivating viable bacteria under a bacterium-propagating condition, and subsequently cultivating the bacteria by contacting with n-amyl alcohol or with a mixture of n-amyl alcohol and a carbon source utilizable by the bacterium under a bacterium propagation-restricting condition; and recovering the copolymer from the bacterial cells wherein said bacterium has a capacity of producing poly-3-hydroxybutyrate and belongs to Genus *Pseudomonas, Athiorhodium, Azotobacter, Spirillum, Methylobacterium, Hyphomicrobium, Ancylocater, Xanthobacter, Paracoccus, Rhizobium, Bradyhizobium, Bacillus, Nocardia, Corynebacterium* or *Rhodococcus*.

* * * * *